Jan. 24, 1967 E. S. BOERNER Plant Pat. 2,701
ROSE PLANT
Filed Dec. 20, 1965
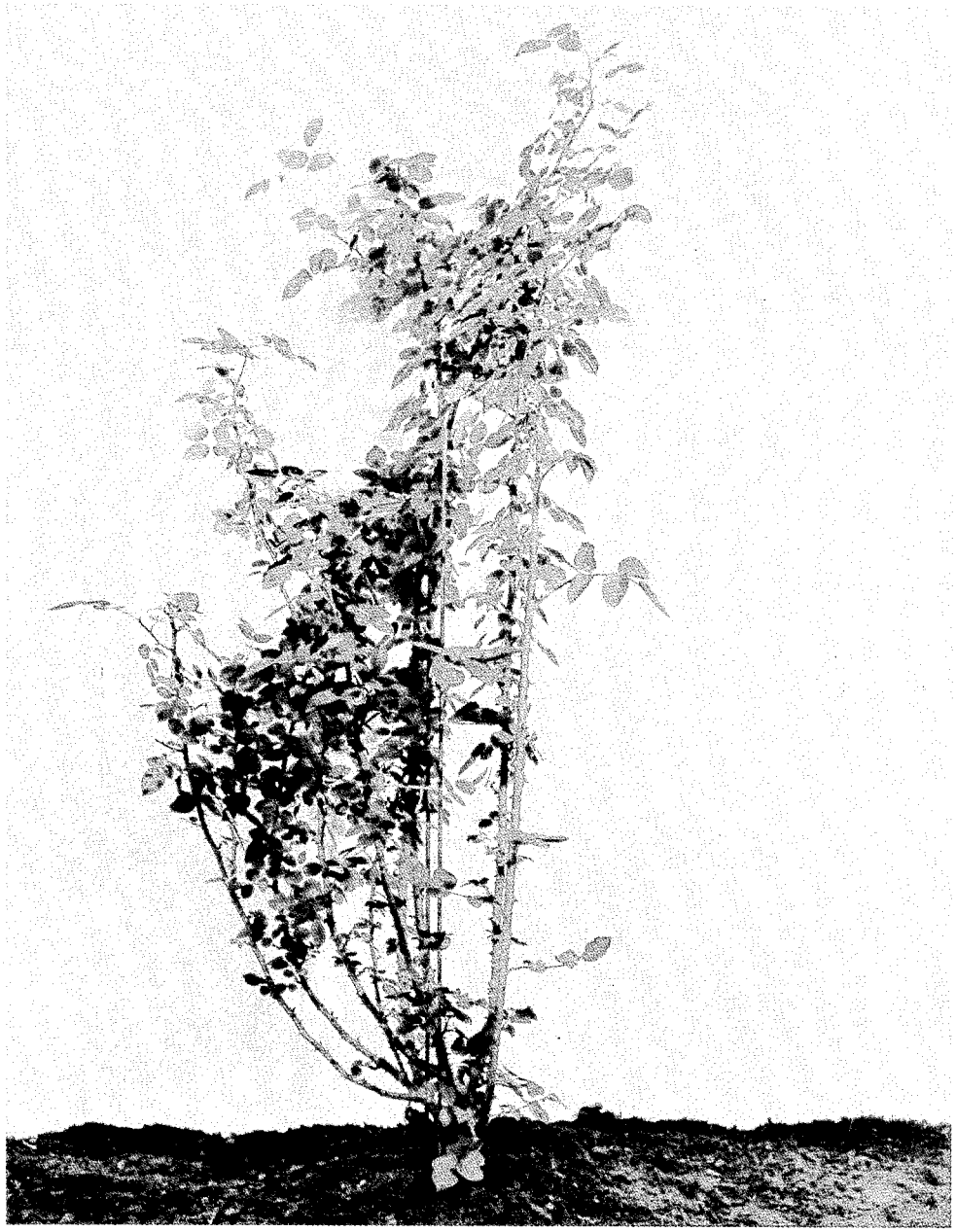
Inventor.
E. S. Boerner
By: Robb & Robb
Attorneys.

United States Patent Office

Plant Pat. 2,701
Patented Jan. 24, 1967

2,701
ROSE PLANT

Eugene S. Boerner, Newark, N.Y., assignor to Jackson & Perkins Company, Newark, N.Y., a corporation of New York Filed Dec. 20, 1965, Ser. No. 515,267
1 Claim. (Cl. Plt.—4)

The present invention relates to a new and distinct variety of rose plant of the climber class, which was discovered by me as a cultivated sport of the hybrid tea rose known as "Tropicana" (Plant Patent No. 1,969), said discovery having been made in the fields of my assignee at Newark, New York.

At the time of my discovery, the parent variety "Tropicana" was being grown extensively in the nursery of my assignee, under my direction and supervision in my capacity as director of research of my assignee. In the course of these operations, my attention was attracted by one particular plant of "Tropicana" which appeared to have departed from the normal bush habit of growth thereof. Upon closer inspection of this plant, I found that it had sported, and as the result thereof, had produced vigorous, upright and long basal shoots. I thereupon took immediate steps to preserve the sport and keep it under close observation. Continued observations of the original sport and its progeny, as produced by budding at both Newark, New York, and Pleasanton, California, conclusively established that its climbing habit of growth was fixed and established and came true through succeeding propagations.

While the new sport otherwise substantially resembles the parent variety "Tropicana," including the general form and color of the foliage and flowers thereof, with the inner surface of the flower petals being Peach Red, lightly overcast with Scarlet, and the reverse petal surface being Peach Red, the plants of the new sport send up long basal shoots which attain a height of from 5 to 6 feet the first year, which in turn send out lateral blooming spikes the second year, with the flowers usually blooming in mass during the month of June in upstate New York. These characteristics represent a unique combination that is definitely different from that of the parent variety, as well as from all other varieties of which I am aware.

Being substantially identical to the parent variety except for the aforementioned distinctions, it is unnecessary to specifically describe the new sport in detail, and the new sport may be considered as otherwise conforming to the detailed description embodied in Plant Patent No. 1,969, issued August 30, 1960, to which reference may be readily had.

For convenience, the accompanying drawing is presented to illustrate the climbing habit of growth of my new variety.

I claim:

A new and distinct variety of rose plant of the climber class, substantially as herein shown and described, characterized particularly as to novelty by being substantially similar to its parent variety "Tropicana" (Plant Patent No. 1,969), but essentially differing therefrom by its climbing habit of growth evidenced by its production of vigorous, upright and long basal shoots which attain a height of from about 5 feet to 6 feet the first year, which in turn produce lateral blooming spikes in the second year, with the flowers usually blooming in mass during the month of June.

No references cited.

ABRAHAM G. STONE, *Primary Examiner.*
ROBERT E. BAGWILL, *Examiner.*